(12) United States Patent
Ondracek

(10) Patent No.: US 7,091,875 B2
(45) Date of Patent: Aug. 15, 2006

(54) WEARABLE REMOTE CONTROL

(76) Inventor: John Ondracek, 3289 Grove St., Denver, CO (US) 80211

( * ) Notice: Subject to any disclaimer, the term of this patent is extended or adjusted under 35 U.S.C. 154(b) by 163 days.

(21) Appl. No.: 10/962,368

(22) Filed: Oct. 6, 2004

(65) Prior Publication Data

US 2006/0071781 A1    Apr. 6, 2006

(51) Int. Cl.
 *G09B 21/00* (2006.01)
(52) U.S. Cl. .............. 340/825.19; 340/573.1; 345/161; 607/9; 607/30; 341/21
(58) Field of Classification Search .......... 340/539.12, 340/573.1, 573.4, 870.01, 870.11, 870.18, 340/825.19; 455/95, 91, 575.1, 575.6; 607/9, 607/30, 32; 345/161; 341/21
See application file for complete search history.

(56) References Cited

U.S. PATENT DOCUMENTS

| | | | |
|---|---|---|---|
| 4,093,037 A | * | 6/1978 | Miller, III .................. 180/316 |
| 4,207,959 A | * | 6/1980 | Youdin et al. .............. 180/167 |
| 4,783,656 A | | 11/1988 | Katz et al. ............. 340/825.19 |
| 4,865,610 A | * | 9/1989 | Muller ........................ 623/24 |
| 5,701,356 A | * | 12/1997 | Stanford et al. ............ 381/385 |
| 6,222,524 B1 | | 4/2001 | Salem et al. ................. 345/157 |
| 6,593,910 B1 | * | 7/2003 | Hester ........................ 345/161 |

\* cited by examiner

*Primary Examiner*—Thomas Mullen
*Assistant Examiner*—Daniel Previl
(74) *Attorney, Agent, or Firm*—Kurt Leyendecker; Leyendecker & Lemire, LLC

(57) ABSTRACT

According to embodiments of the present invention, a wearable remote control for controlling one or more devices comprises a mounting base coupled with a garment. A retainer base is coupled with the mounting base on an outside of the garment. A multi-directional joint is coupled with the retainer base. A main support extends from the multi-directional joint on an opposite side of the multi-directional joint from the retainer base. An input device is coupled with an end of the main support opposite the multi-directional joint. A main support retainer extends from the retainer base and is adapted to engage and retain the main support in a non-use position in response to a user moving the garment.

20 Claims, 7 Drawing Sheets

WEARABLE REMOTE CONTROL

FIELD OF THE INVENTION

The invention relates generally to the field of remote control devices. More particularly, the invention relates to a wearable remote control for hands free control of one or more devices.

BACKGROUND OF THE INVENTION

For some individuals, a remote control for controlling one or more electrical or electronic devices is more than a convenience, it is a necessity. Those individuals who are paraplegics and quadriplegics relay upon remote controls of various types for controlling devices that they cannot otherwise manipulate. For example, wheelchairs may be fitted with a remote control for controlling movement of the chair. The chair may be controlled by way of a pressure pad, joystick or other input device.

However, the remote controls commonly in use are mounted in fixed positions on the chair. For example, a joystick used to control a wheelchair may be mounted on the arm of the chair or on a post or extension that holds the joystick in a fixed position relative to the user's head. As such, the user must move towards the input device to engage and manipulate it. This arrangement may be awkward, inconvenient, and difficult to use. It is with respect to these considerations and others that the present invention has been made.

SUMMARY OF THE INVENTION

In accordance with the present invention, the above and other problems are solved by a wearable remote control for controlling one or more devices. The remote control allows the user to move an input device of the control between an in-use position and a non-use position without using his hands.

According to aspects of the present invention, the remote control comprises a mounting base coupled with a garment. A retainer base is coupled with the mounting base on an outside of the garment and a multi-directional joint is coupled with the retainer base. A main support extends from the multi-directional joint on an opposite side of the multi-directional joint from the retainer base. An input device is coupled with an end of the main support opposite the multi-directional joint. A main support retainer extends from the retainer base and is adapted to engage and retain the main support in a non-use position in response to a user moving the garment.

In accordance with other aspects, the present invention relates to a wearable remote control for controlling one or more devices. The remote control has a mounting base coupled with a garment. A mounting post extends from the mounting base, away from the garment and a retainer base, defining a cavity, slideably receives the mounting post in the cavity. A multi-directional joint is coupled with the retainer base. A main support extends from the multi-directional joint on an opposite side of the multi-directional joint from the retainer base. An input device is coupled with an end of the main support opposite the multi-directional joint. A main support retainer extends from the retainer base and is adapted to engage and retain the main support in a non-use position in response to a user moving the garment.

In accordance with still other aspects, the present invention relates to a wearable remote control for controlling one or more devices, the remote control comprising a mounting base coupled with a garment. A mounting post extends from the mounting base, away from the garment. A retainer base, defining a cavity, is adapted to slideably receive the mounting post in the cavity. A multi-directional joint is coupled with the retainer base. The multi-directional joint comprises a first pivot adapted to move the main support in a first direction laterally in front of the user and a second pivot adapted to move the main support in a second direction substantially perpendicular to the first direction. A main support extends from the multi-directional joint on an opposite side of the multi-directional joint from the retainer base. The main support defines a cavity at the end of the main support opposite the multi-directional joint. An input device support extension slideably engages the cavity in the end of the main support opposite the multi-directional joint. A bite plate is coupled with an end of the input device support extension opposite the main support. An inter-oral joystick is coupled with the bite plate on a side of the bite plate opposite the input device support extension. A main support retainer extends from the retainer base and is adapted to engage and retain the main support in a non-use position in response to a user moving the garment.

Other features of the present invention will be apparent from the accompanying drawings and from the detailed description that follows.

DETAILED DESCRIPTION

Figure 1:
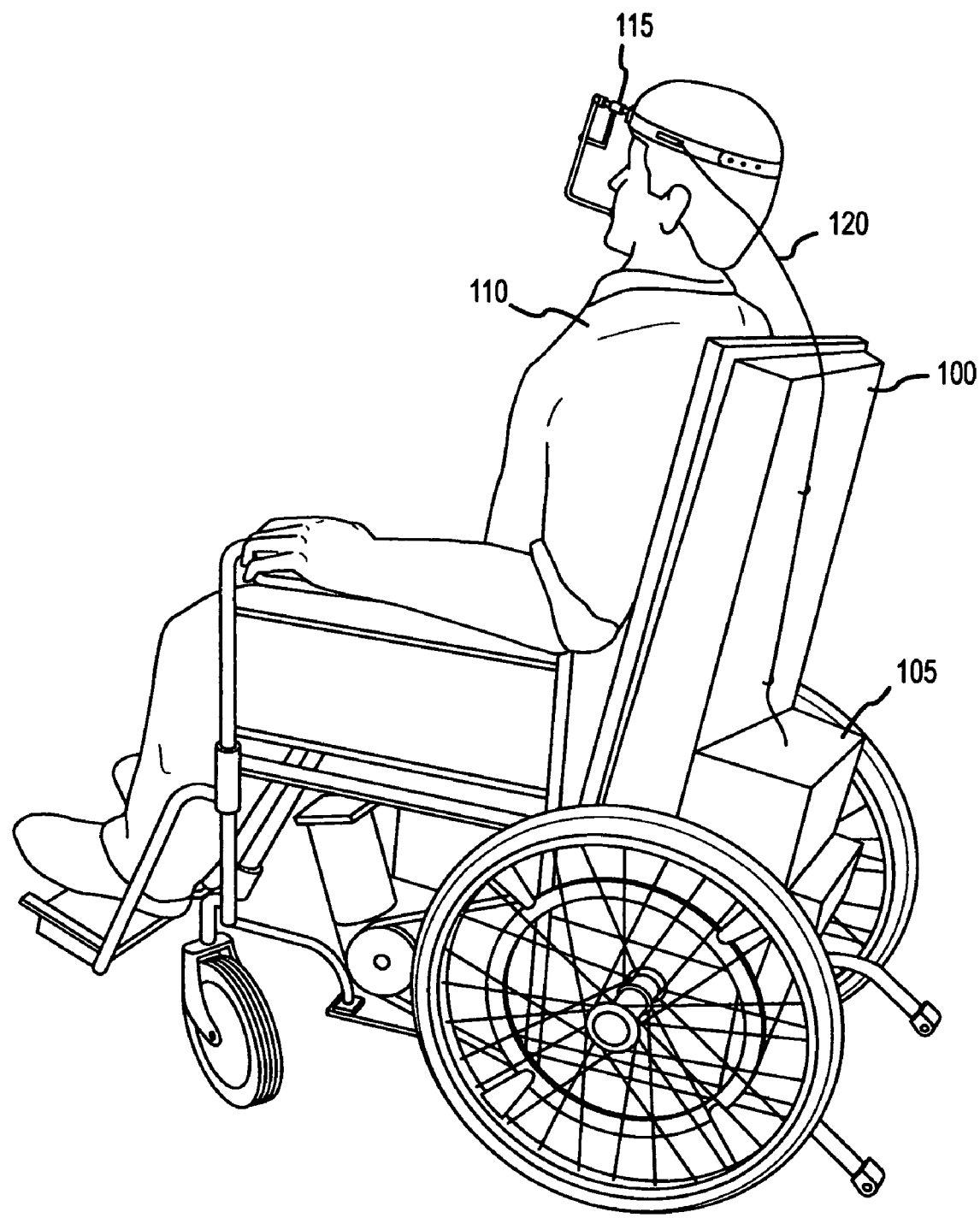
FIG. 1 illustrates one possible application for wearable remote controls according to embodiments of the present invention.

A method and apparatus are described for a wearable remote control. According to embodiments of the present invention, the wearable remote control allows a user to move an input device of the remote control between an in-use position and a non-use position by moving the garment to which the wearable remote control is attached. In this way, the user can shift the input device between positions as is convenient without the use of his hands.

Terminology

Various terms used throughout this description will be defined as follows.

The term "or" as used in this specification and the appended claims is not meant to be exclusive rather the term is inclusive meaning "either or both".

References in the specification to "one embodiment", "an embodiment", "a preferred embodiment", "an alternative embodiment", "one variation", "a variation" and similar phrases mean that a particular feature, structure, or characteristic described in connection with the embodiment or variation is included in at least an embodiment or variation of the invention. The phrase "in one embodiment", "in one variation" or similar phrases as used in various places in the specification are not necessarily meant to refer to the same embodiment or the same variation.

The term "couple" or "coupled" as used in this specification and the appended claims refers to either an indirect or direct connection between the identified elements, components or objects. Often the manner of the coupling will be related specifically to the manner in which the two coupled elements interact.

The term "indicia" refers to any words, phrases, numbers, logos, pictures and/or symbols that are intended by an originator of the indicia to have meaning to a viewer thereof.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

The term "cutout" as used herein refers to a hole or space in the sheet material that is substantially surrounded by remaining sheet material excepting a slot, a slit or some similar feature extending from an outside edge to the cutout. In contrast, the term "cutaway" as used herein refers to an area wherein sheet material is removed (or could have been removed) and wherein at least one outside edge of the remaining sheet material directly abuts the cutaway.

Importantly, while embodiments of the present invention will be described with reference to a headband mounted wearable remote control for controlling a wheelchair, the method and apparatus described herein are equally applicable to other types of garments and other types of devices. For example, various other embodiments of the invention may be used with other types of garments such as a necklace, scarf, or collar or a shirt, jacket, vest, coat, etc. The wearable remote control may also be used to control a wide variety of devices other than a wheelchair. For example, the remote control may be used to control a television, telephone, stereo, various types of appliances, computers, etc.

FIG. 1 illustrates one possible application for wearable remote controls according to embodiments of the present invention. This example shows a user 110 with a wearable remote control 115 for controlling a wheelchair 100. Here, the remote control 115 is in the form of a headband that can be worn by the user 110. Other types of garments may be also be used with various embodiments of the present invention. For example, various other types of headwear such as a hat, helmet, visor, bandanna, etc. may be used in place of a headband. Further, garments other than headwear may also be used. For example, it is conceived that the remote control may be adapted to the collar, shoulder, chest or other part of a shirt, vest, jacket, coat, etc. Additionally, while a wheelchair 100 is shown here, other types of devices may also be controlled by various embodiments of the present invention. For example, a television, radio, telephone, computer, lights, appliances, etc. may also be controlled. Further, as will be described below, more than one device or even type of device may be controlled by the wearable remote control.

As shown in FIG. 1, the wearable remote control 115 is electrically connected with a controller 105 for the wheelchair 100 via an electrical wire 120. Alternatively, the wearable remote control 115 may be connected to the wheelchair 100 or other devices via a wireless connection. For example, the wearable remote control 115 may be connected to a wireless local area network (WLAN) within the user's home. Through the WLAN, the user 110 may have access to and be able to control a wide range of devices and appliances.

The wearable remote control 115 also includes an input device (not shown here) that is placed into the user's mouth. As will be described below, the input device may comprise an inter-oral joystick or other similar device that may be manipulated by the user 110 without the use of his hands.

As will be described below with reference to FIGS. 2–5, the wearable remote control 115 allows the user 110 to move the input device away from the mouth to a non-use position simply by moving the garment to which it is attached. That is, as shown in FIG. 1, the user 110 can move the input device away from his mouth by moving his head to cause the input device to swing to a non-use position where it will be retained until the user 110 moves his head again to return the input device to the in-use position at or near his mouth. This way, the user 110 has control of the remote control as needed and may move it away when not in use without the use of his hands.

Figure 2:
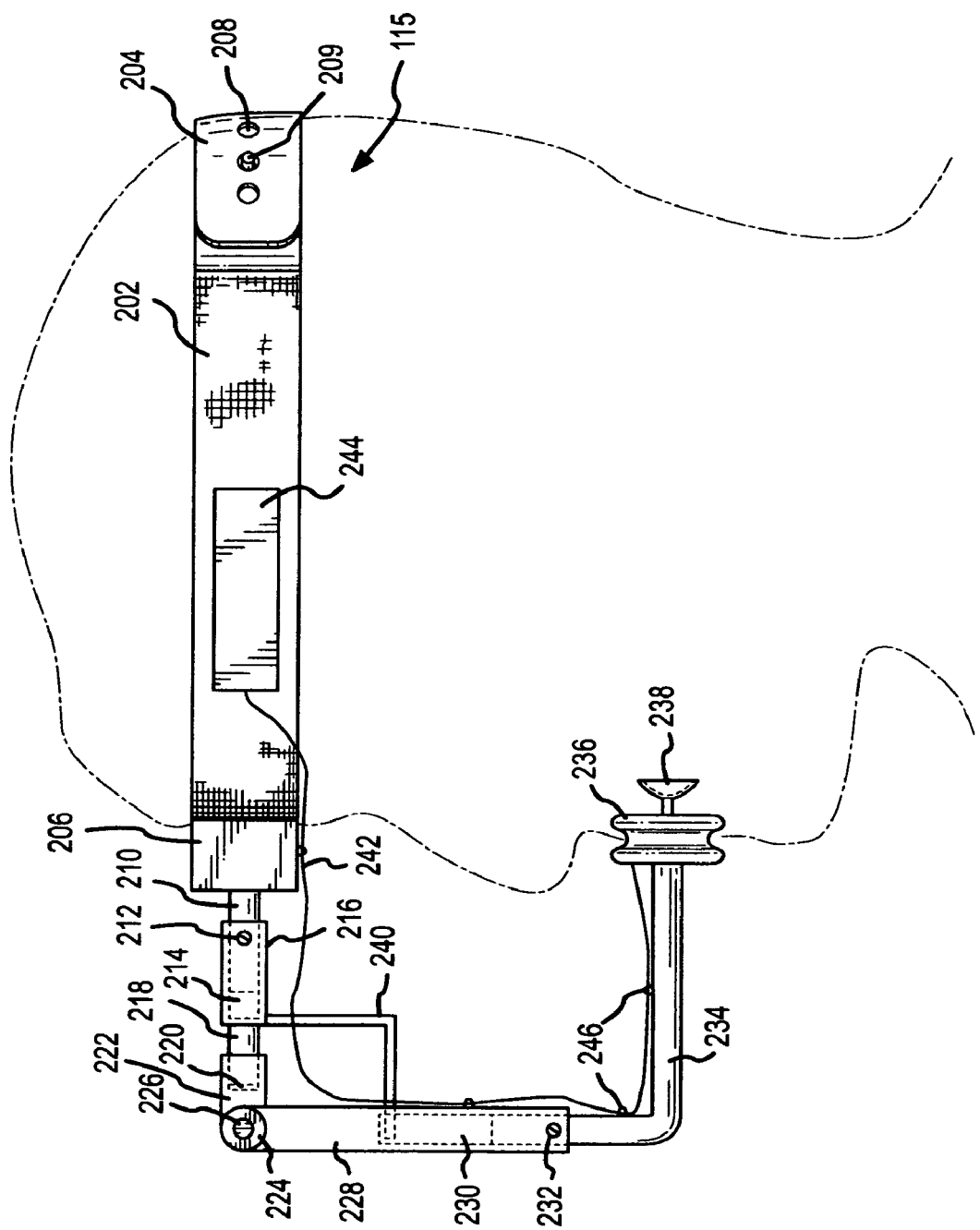
FIG. 2 is a side view of a wearable remote control according to one embodiment of the present invention.

FIG. 2 is a side view of a wearable remote control according to one embodiment of the present invention. In this example, the wearable remote control 115 is shown in the form of a headband 202 as in FIG. 1. As noted above, other types of headwear such as hats, helmets, visors, bandannas, dew rags, etc. are considered to be equally applicable for use with a the wearable remote control 115. The headband 202, or other garment, may be made from a wide range of materials as is typically used for similar garments. For example, a headband 202 as shown here may be made of cloth, vinyl, leather, elastic, etc.

The headband 202 shown in FIG. 2 also includes a size adjustment portion 204. The size adjustment portion 204 can comprise, for example, a series of holes 208 and fasteners 209 as is commonly found on baseball caps. Alternatively, other types of size adjustment mechanisms may be used. For example, hook and loop fasteners like Velcro®, snaps, buttons, belts, slides, and other types of fasteners and adjusters may be used.

The headband 202 also includes a mounting base portion 206. The mounting base 206 provides a rigid or semi-rigid base to which the rest of the wearable remote control 115 may be connected with the headband 202 or other garment. The material from which the mounting base 206 is made may vary depending upon the weight of the other portions of the remote control 115 that will be supported by the mounting base 206.

Extending from the mounting base 206 may be an optional mounting post 210. The mounting post 210, if used, may be constructed as a single unit with the mounting base 206 or may be coupled with the mounting base 206 via adhesives or fasteners of various types.

As shown in FIG. 2, a retainer base 216 is coupled with the mounting post 210. The retainer base 216 defines a cavity 214 or channel adapted to receive the mounting post 210 and allow the retainer base 216 to slide along the mounting post 210 to provide some size adjustment to the remote control 115. A set screw 212 or other fastener may also be located in the body of the retainer base 216 to lock the retainer base 216 to a particular position on the mounting post 210. Alternatively, if no mounting post 210 is used, the retainer base 216 may be mounted on or connected with the mounting base 206 of the headband 202.

In this example, an optional coupling 218 extends from the front of the retainer base 216. The coupling 218 and retainer base 216 may be constructed as a single unit or the coupling 218 may be connected with the retainer base 216 by adhesives, welding, fasteners or other means. The coupling 218 can provide a means by which the remainder of the remote control 115, such as first pivot 222, may be connected to the retainer base 216 and headband 202. In this example, the first pivot body 222 defines a cavity 220 or channel adapted to accept the end of the coupling 218. Alternatively, the remainder of the remote control may be connected directly to the retainer base 216. For example, the first pivot body 222 may be connected to the retainer base 216 by adhesives, welding, fasteners, or other means.

Mounted to the coupling 218, if any, or the retainer base 216, if no coupling 218 is used, is a multi-directional joint. As illustrated in FIG. 2, the multi-directional joint consists of a first pivot 222 and a second pivot 224. As will be seen, the first pivot 222 rotates about a fastener (not shown here) or shaft in a first direction while the second pivot 224 rotates about a fastener 226 or shaft in a second direction generally perpendicular to the first direction.

Extending from the second pivot 224 is a main support 228 to support an input device 238 at an end of the main support 228 opposite the multi-directional joint. Details of the input device 238 and other features will be discussed further below. The first pivot 222 allows the main support to move in a first direction substantially laterally (i.e., from right to left or vise versa) in front of the users face when the headband 202 is moved or tilted from side to side. The second pivot 224 allows the main support 228 to move in a second direction relative to the first direction. According to one embodiment of the present invention, this second direction may be substantially perpendicular to the first direction. Therefore, the second pivot 224 may allow the main support 228 to move toward or away from the user in response to the user tipping his head forward or backward. In this way, the user can control the position of the main support 228 and therefore the input device 238 by moving his head.

Furthermore, a retainer 240 extends from the retainer base 216 and is positioned to engage and retain the main support 228 in a non-use position in response to a user moving the garment. That is, by moving his head, for example forward, to the right, and then back, the user can move the main support 228 and input device 238 away from his mouth to be caught and retained on the retainer 240. Moving his head forward, to the left, and back will then move the main support 228 and input device 238 back to an in-use position near the user's mouth.

As illustrated in FIG. 2, the remote control 115 also includes an optional input device support extension 234 disposed between the main support 228 and the input device 238. The support extension 234 extends from the main extension 228 and positions the input device 238 in a location that is easy for the user to reach when in an in-use position. As shown here, the main support 228 defines a cavity 230 at an end of the main support 228 opposite the second pivot 224. The cavity 230 is adapted to slideably receive the end of the support extension 234 opposite the input device 238. The support extension 234 may be secured in the channel 230 of the main support 228 by a set screw 232 or other means. In this way, the remote control 115 may be adjusted to accommodate the size of the user.

The input device 238 may be any of a variety of input devices such as an inter-oral joystick, as shown here, a blow tube, or other type of sensor. Also shown in FIG. 2 is an optional bite plate 236 disposed between the support extension 234 and the input device 238. The bite plate 236, if used, helps to retain and stabilize the input device 238 while it is being manipulated by the user.

The input device 238 may be electrically coupled with a control module 244 via an electrical wire 242 or conductor. The wire 242 may pass through the bite plate 236, if any, and be secured to the support extension 234, main support 228, headband 202 and/or other parts by one or more cable stays 246, cleats, ties or other fasteners.

As shown here, the control module 244 may be mounted on the headband 202. Alternatively, the control module 244 may be located in a wide variety of places. For example, the control module may be built into the bite plate, mounted on another part of the remote control 115, located in a wheelchair, etc. Regardless of its exact location, the control module 244 receives and interprets input signals from the input device 238. The control module 244 then, based on the signals from the input device 238, controls one or more devices. The control module 244 may, for example be coupled to a home Wireless Local Area Network (WLAN) or other network in the user's home. Through the WLAN, the user may have access to and be able to control a wide range of devices and appliances. Alternatively, the control module 244 may be coupled with a device such as a wheelchair via an electrical wire or conductor as shown in FIG. 1. According to one embodiment, the control module 244 may be coupled with a control module in the wheelchair which, in turn, includes a WLAN card for coupling the remote control with one or more other devices.

Figure 3:
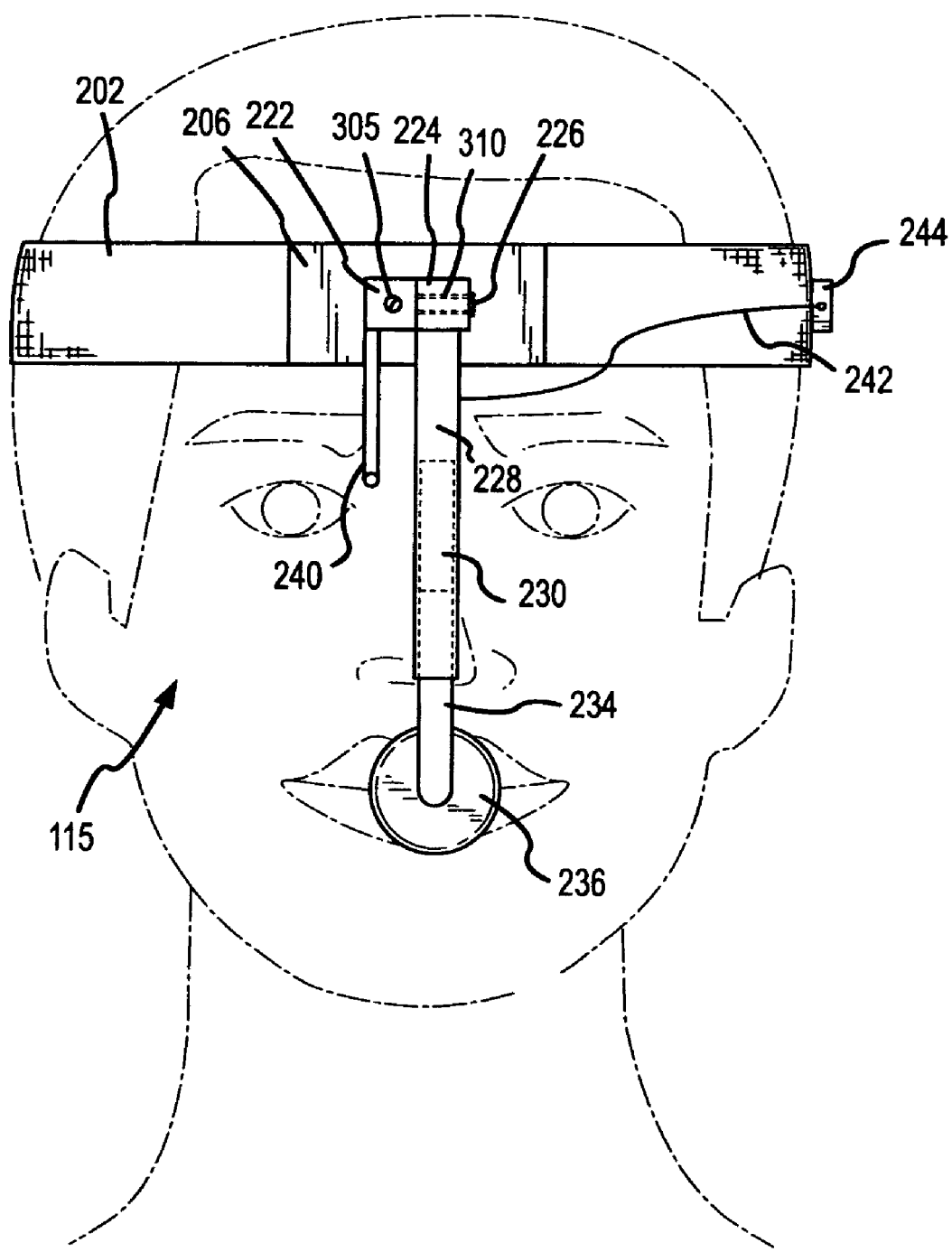
FIG. 3 is a front view of a wearable remote control according to the embodiment illustrated in FIG. 2 with the input device in a first, in-use position.

FIG. 3 is a front view of a wearable remote control according to the embodiment illustrated in FIG. 2 with the input device in a first, in-use position. Visible in this view is the headband 202 with the mounting base 206. The first pivot 222 of the multi-directional joint is mounted on the mounting base 206 via the mounting post 210, retainer base 216, and coupling 218 as discussed above with reference to FIG. 2. According to one embodiment of the present invention, the first pivot 222 may be coupled with the coupling 218, if any, or retainer base 216 via a fastener 305 such as a screw, bolt, rivot, pin, etc.

Similarly, the second pivot 224 may be coupled with the first pivot 222 via another fastener 226 which may also be a screw, bolt, rivot, pin, etc. As can be seen here, the body of the second pivot 224 defines a hole 310 through which the fastener 226 may pass to be secured to the first pivot 222. For example, a bolt used as the fastener 226 for the second pivot 224 may pass through the hole in the body of the second pivot 224 and be threaded into matching threads in the body of the first pivot 222. Further, the body of the second pivot 224, while retained by the fastener 226, allows the second pivot 224 to rotate about the fastener 226 providing a range of motion in the direction toward or away from the users face as described above.

Also visible in FIG. 3 is the main support 228, the support extension 234, and the bite plate 236. The retainer 240 is also visible extending from the bottom of the retainer base (not visible in this view). When the user moves the headband 202 by tipping his head forward and to the right, the main support 228 pivots about the fastener 226 and the first pivot 222 rotates about fastener 305. However, the retainer 240 does not move as the retainer base 216 is fixed to the headband 202 via the mounting post 210 as shown in FIG. 2

Figure 4:
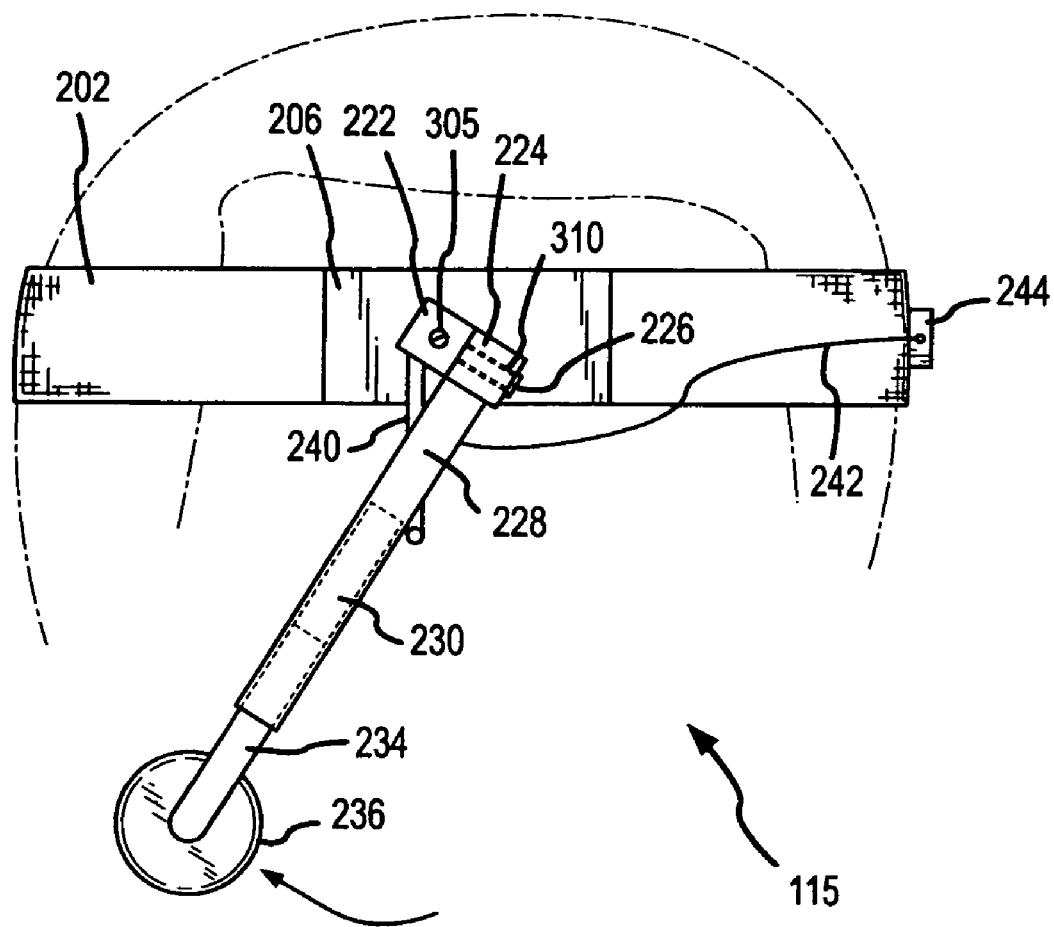
FIG. 4 is a front view of a wearable remote control according to the embodiment illustrated in FIG. 2 with the input device retained in a second, non-use position.

FIG. 4 is a front view of a wearable remote control according to the embodiment illustrated in FIG. 2 with the input device pivoted to a second, non-use position. This view shows the headband 202 with mounting base 206. Also shown are the first pivot 222, second pivot 224, main support 228, support extension 234, and bite plate 236. In this example, the headband 202 has been moved by the user tipping his head forward and to his right and then upright again. This causes the second pivot 224 to rotate away from the user's face and the first pivot 222 to rotate to the user's right. As a result, the main support 228 and therefore the input device moves away from the user's face and to his right. Once the main support 228 has moved far enough, the user returns his head to an upright position, which causes the main support 228 to engage the retainer 240. The retain 240 then holds the main support 228 in this non-use position until the user tips his head forward, causing the second pivot 224 and the main support 228 to rotate until the main support 228 clears the retainer, allowing the main support 228 and input device to return to the in-use position in front of the user's face.

As shown in FIG. 4, the input device is away from the user's mouth. However, the main support 228, as illustrated, may partially block the user's vision. Therefore, in an alternative embodiment, the retainer 240 and/or main support 228 may be configured to place the main support 228 out of the user's field of vision. For example, the retainer 240 may be shaped to place the main support 228 further to the user's right when in the non-use position. Alternatively, the main support 228 may be shaped to avoid the user's field of vision when it is in the non-use position.

Figure 5:
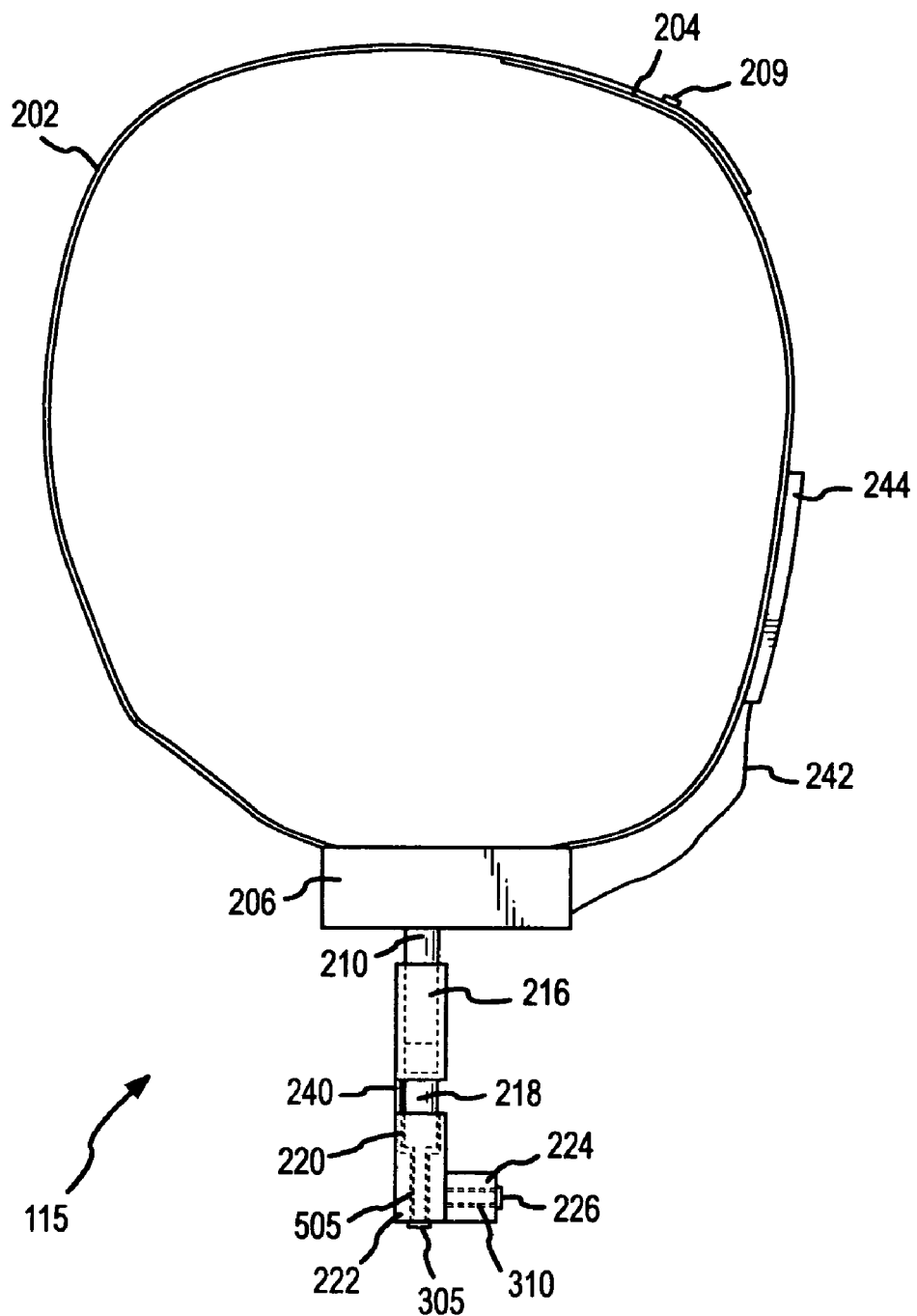
FIG. 5 is a top view of wearable remote control according to the embodiment illustrated in FIG. 2.

FIG. 5 is a top view of wearable remote control according to the embodiment illustrated in FIG. 2. This view shows the headband 202 including the mounting base 206, size adjustment portion 204 and adjustment fastener 209. The control module 244 can be mounted on the side of the headband 202 or in any of a number of other locations as described above and may be electrically coupled with the input device (not visible in this view) via signal wire 242 or other means.

Also shown in this view is optional mounting post 210 extending from mounting base 206. The retainer base 216 is coupled with the mounting post 210 and optional coupling 218. The first pivot 222 is coupled with the optional coupling 218. As noted above, rather than mounting on the coupling 218, the first pivot 222 may alternatively be coupled with the retainer base 216.

The body of the first pivot 222 defines a cavity 505 adapted to accept the coupling 218 or end of the retainer base 216. Additionally, the cavity 505 is adapted to allow a fastener 305 such as a bolt, screw, rivot, pin, etc. to pass through the body of the first pivot 222 to be secured to the retainer base 216 or coupling 218. For example, a bolt used as the fastener 305 for the first pivot 222 may pass through the hole in the body of the first pivot 222 and be threaded into matching threads in the body of the retainer base 216 or coupling 218. Further, the body of the first pivot 222, while retained by the fastener 305, allows the first pivot 222 to rotate about the fastener 305 providing a range of motion laterally (i.e., side to side) in front of the users face as described above.

Similarly, the second pivot 224 may be coupled with the first pivot 222 via another fastener 226 which may also be a screw, bolt, rivot, pin, etc. As can be seen here, the body of the second pivot 224 defines a cavity 310 through which the fastener 226 may pass to be secured to the first pivot 222. For example, a bolt used as the fastener 226 for the second pivot 224 may pass through the cavity 310 in the body of the second pivot 226 and be threaded into matching threads in the body of the first pivot 222. Further, the body of the second pivot 224, while retained by the fastener 226, allows the second pivot 224 to rotate about the fastener 226 providing a range of motion in the direction toward or away from the users face as described above.

Figure 6:
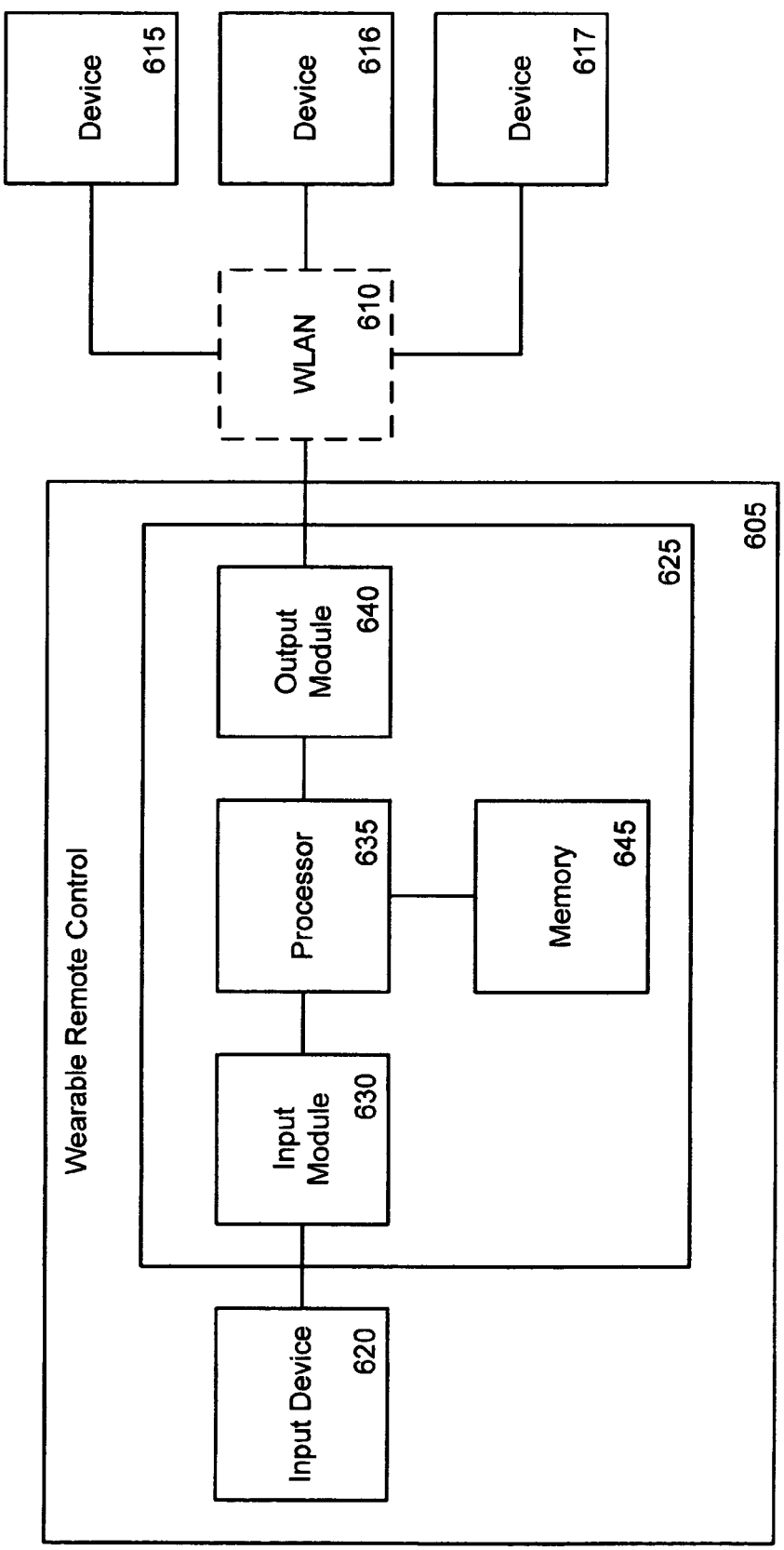
FIG. 6 is a block diagram illustrating the primary electrical components of a system for controlling one or more devices using a wearable remote control according to one embodiment of the present invention.

FIG. 6 is a block diagram illustrating the primary electrical components of a system for controlling one or more devices using a wearable remote control according to one embodiment of the present invention. This system 600 comprises the wearable remote control 605, an optional Wireless Local Area Network (WLAN) 610 or some other electrical connection, and a number of devices 615–617. The wireless remote control 605 comprises an input device 620 and a control module 625. The input device 620, as discussed above, can be any of a variety of possible input devices such as an inter-oral joystick, a blow tube, a microphone, etc. Typically, the input device 620 is coupled with the control module 625 via one or more electrical conductors. Feedback from the input device 620 based on the user's manipulation of the input device 620 is sent to the control module 625 via the conductor.

The control module 625 includes an input module 630. The input module 630 comprises circuitry for converting the feedback signals from the input device 620 to levels and conditions suitable for processing by the control module 625. For example, since the signal from the input device 620 may be an analog signal indicating the position if the device, the input module 630 may comprise buffers, an analog-to-digital (A/D) converter, amplifiers and/or other elements. Regardless of the exact nature of the input module 630, output signals from the input module 630 are then supplied to the processor 635 of the control module 625.

The processor 635 can comprise a microprocessor or similar device for executing software instructions stored in memory 645. Generally speaking, the instructions stored in memory 645 and executed by processor 635 cause the processor 635 to interpret signals from the input module 630 and, based on these signals, provide appropriate outputs for controlling one or more devices 615–617. For example, the user may "click" or indicate a device selection on an inter-oral joystick used as an input device by pressing the joystick straight forward with his tongue. This signal can be interpreted accordingly by the processor 635. Once a device is selected, further manipulation of the input device 620 can be interpreted accordingly by the processor 635 to determine commands to be sent to the selected device. Additional details of these processes will be discussed below with reference to FIG. 7.

Signals generated by the processor 635 for controlling the one or more devices 615–617 are output from the processor 635 to the output module 640. The output module 640 conditions the signals from the processor 635 and prepares them for transmission from the wearable remote control 605 to the devices 615–617. For example, if the output signals from the wearable remote control 605 are transmitted to the devices 615–617 via an optional WLAN 610, the output module 640 may comprise a wireless network card or module. Alternatively, if output signals from the wearable remote control 605 are transmitted to the devices 615–617 via hardwired electrical conductors, output module 640 may comprise amplifiers, timing circuits, multiplexors, and/or other circuits to condition the output signals for transmission to the devices 615–617. It is also contemplated that more than one type of transmission media may be used by the wearable remote control 605. For example, the wearable remote control 605 may communicate with some devices such as appliances, computers, etc. via a WLAN and another device such as a wheelchair via hardwired electrical conductors. Therefore, output module 640 may comprise a number of outputs of different types.

Signals output from the output module 640 of the wearable remote control 605 are transmitted via a medium such as optional WLAN 610 or hardwired conductors to devices 615–617. The devices 615–617 receive the signals from medium and each device 615–617 responds accordingly to signals addressed to that particular device. That is, each device may contain a processor or other hardware for receiving signals from the remote control 605, determining, based on an address or other identifier, which signals are intended for that device, and then controlling the device based on those signals.

Figure 7:
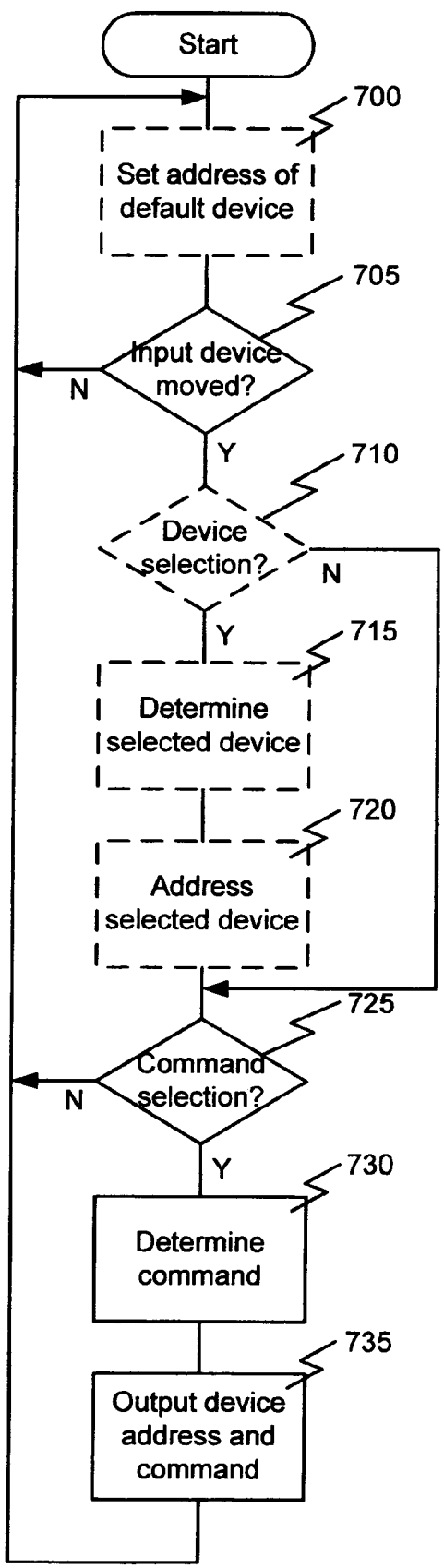
FIG. 7 is a flowchart illustrating control of one or more devices using a wearable remote control according to one embodiment of the present invention.

FIG. 7 is a flowchart illustrating control of one or more devices using a wearable remote control according to one embodiment of the present invention. In this example, processing begins with optional initiation operation 700. Initiation operation 700, if used, comprises setting the address of the default device. That is, if more than one device is to be controlled by the wearable remote control, one of the devices may be predetermined to be the default device. Therefore, absent a user selection of a device, commands generated in response to user manipulation of the input device may be applied to the default device. Alternatively, if only one device is controlled by the wearable remote control, there is no need to differentiate commands between devices and therefore no need to set a default device. According to yet another alternative, no default may be set. In such a case, processing may ignore commands until a device is selected.

Next, query operation 705 comprises determining whether the input device has moved. That is, a determination is made based on the feedback signals from the input device as to whether the user has manipulated or moved the input device. If movement is detected, processing continues with optional query operation 710.

Query operation 710 comprises determining whether the movement of the input device constitutes the selection of a device. For example, if the input device is an inter-oral joystick, selection of a device may be accomplished by pressing the joystick forward with the tongue to affect a "click" or selection. If only one device is controlled by the wearable remote control, this operation, as well as subsequent determination operation 715 and set operation 720, may be considered optional. If a determination is made that the input device movement is not a device selection operation, control jumps to determination operation 725. However, if a determination is made that the input device movement constitutes a device selection operation, processing continues with determination operation 715.

Determination operation 715 comprises determining the selected device. That is, a determination is made as to which device, if more than one is available, is being selected by the user. This determination may be based on a number of criteria but may be related to the type of input device used. For example, if an inter-oral joystick is used as the input device, selection of a device may be accomplished by repeated pressing or clicking of the joystick. Selection of a first device may therefore be accomplished by clicking the joystick once while selection of a second device may be accomplished by clicking the joystick twice and so on. Once a determination is made as to which device is selected, processing continues with set operation 720.

Set operation 720 comprises setting the address of the selected device. That is, an IP address, network location, channel, or other identifying information for addressing a particular device is determined for the device selected. Such information may be stored in memory of the remote control and retrieved from a table or other data structure. Processing then continues with query operation 725.

Query operation 725 comprises determining whether the input device movement comprises the selection of a command. This determination may be based on a number of criteria but may be related to the type of input device used. For example, if an inter-oral joystick is used as the input device, selection of a particular command may be based on a directional movement of the joystick. Processing then continues with determination operation 730.

Determination operation 730 comprises determining which command has been selected. This determination may be based on a number of criteria but may be related to the type of input device used. For example, if an inter-oral joystick is used as the input device, selection of a particular command may be based on a directional movement of the joystick. Moving the joystick to the right may therefore indicate movement of the selected device to the right, movement of a mouse on a computer display, increase or decrease of a stereo or television volume, etc. The determination may be made by correlating the movement detected with a database, list, table, or other data structure for the selected device. Processing then continues with output operation 735.

Output operation 735 comprises sending the address for the selected device, if any, and the command to the one or more devices connected with the wearable remote control.

The various preferred embodiments and variations thereof illustrated in the accompanying Figures and/or described above are merely exemplary and are not meant to limit the scope of the invention. It is to be appreciated that numerous variations of the invention have been contemplated as would be obvious to one of ordinary skill in the art with the benefit of this disclosure. All variations of the cover that read upon the appended claims are intended and contemplated to be within the scope of the invention.

What is claimed is:

1. A wearable remote control for controlling one or more devices, the remote control comprising:
   a mounting base coupled with a garment;
   a mounting post extending from the mounting base, away from the garment;
   a retainer base defining a cavity and adapted to slideably receive the mounting post in the cavity;
   a multi-directional joint coupled with the retainer base;
   a main support extending from the multi-directional joint on an opposite side of the multi-directional joint from the retainer base;
   an input device coupled with an end of the main support opposite the multi-directional joint;
   a main support retainer extending from the retainer base and adapted to engage and retain the main support in a non-use position in response to a user moving the garment.

2. The remote control of claim 1, wherein the garment comprises a headband.

3. The remote control of claim 1, wherein the multi-directional joint comprises a first pivot adapted to move the main support in a first direction laterally in front of the user.

4. The remote control of claim 3, wherein the multi-directional joint further comprises a second pivot adapted to move the main support in a second direction substantially perpendicular to the first direction.

5. The remote control of claim 1, wherein the main support further defines a cavity at the end of the main support opposite the multi-directional joint.

6. The remote control of claim 5, further comprising an input device support extension disposed between the main support and the input device and slideably engaging the cavity in the end of the main support opposite the multi-directional joint.

7. The remote control of claim 1, wherein the input device comprises an inter-oral joystick.

8. The remote control of claim 7, further comprising a bite plate disposed between an end of the input device support extension opposite the main support and the inter-oral joystick.

9. A wearable remote control for controlling one or more devices, the remote control comprising:
   a mounting base coupled with a garment;
   a retainer base coupled with the mounting base on an outside of the garment;
   a multi-directional joint coupled with the retainer base;
   a main support extending from the multi-directional joint on an opposite side of the multi-directional joint from the retainer base;
   an input device coupled with an end of the main support opposite the multi-directional joint;
   a main support retainer extending from the retainer base and adapted to engage and retain the main support in a non-use position in response to a user moving the garment.

10. The remote control of claim 9, further comprising a mounting post disposed between the mounting base and the retainer base and extending from the mounting base, away from the garment.

11. The remote control of claim 10, wherein the retainer base further defines a cavity adapted to slideably receive the mounting post.

12. The remote control of claim 10, wherein the multi-directional joint further comprises a second pivot adapted to move the main support in a second direction substantially perpendicular to the first direction.

13. The remote control of claim 9, wherein the garment comprises a headband.

14. The remote control of claim 9, wherein the multi-directional joint comprises a first pivot adapted to move the main support in a first direction laterally in front of the user.

15. The remote control of claim 9, wherein the main support further defines a cavity at the end of the main support opposite the multi-directional joint.

16. The remote control of claim 15, further comprising an input device support extension disposed between the main support and the input device and slideably engaging the cavity in the end of the main support opposite the multi-directional joint.

17. The remote control of claim 9, wherein the input device comprises an inter-oral joystick.

18. The remote control of claim 17, further comprising a bite plate disposed between an end of the input device support extension opposite the main support and the inter-oral joystick.

19. A wearable remote control for controlling one or more devices, the remote control comprising:
   a mounting base coupled with a garment;
   a mounting post extending from the mounting base, away from the garment;
   a retainer base defining a cavity adapted to slideably receive the mounting post;
   a multi-directional joint coupled with the retainer base, the multi-directional joint comprising a first pivot adapted to move the main support in a first direction laterally in front of the user and a second pivot adapted to move the main support in a second direction substantially perpendicular to the first direction;
   a main support extending from the multi-directional joint on an opposite side of the multi-directional joint from the retainer base wherein the main support defines a cavity at the end of the main support opposite the multi-directional joint;
   an input device support extension slideably engaging the cavity in the end of the main support opposite the multi-directional joint;
   a bite plate coupled with an end of the input device support extension opposite the main support;
   an inter-oral joystick coupled with an the bite plate on side of the bite plate opposite the input device support extension; and
   a main support retainer extending from the retainer base and adapted to engage and retain the main support in a non-use position in response to a user moving the garment.

20. The remote control of claim 19, wherein the garment comprises a headband.

* * * * *